US005869608A

United States Patent [19]

Caldwell et al.

[11] Patent Number: 5,869,608

[45] Date of Patent: Feb. 9, 1999

[54] **NUCLEOTIDE AND AMINO ACID SEQUENCES OF THE FOUR VARIABLE DOMAINS OF THE MAJOR OUTER MEMBRANE PROTEINS OF *CHLAMYDIA TRACHOMATIS***

[75] Inventors: Harlan D. Caldwell; Yuan Ying; You-Xun Zhang, all of Hamilton; Nancy G. Watkins, Victor, all of Mont.

[73] Assignee: The United States of America as represented by the Department of Health and Human Services, Washington, D.C.

[21] Appl. No.: 853,359

[22] Filed: Mar. 16, 1992

Related U.S. Application Data

[63] Continuation of Ser. No. 324,664, Mar. 17, 1989, abandoned.

[51] Int. Cl.$^6$ ......................... C07K 14/295; C12N 15/31

[52] U.S. Cl. .................. 530/350; 424/185.1; 424/263.1; 536/23.7

[58] Field of Search .................................... 530/300, 324, 530/325, 326, 350; 424/88, 263.1, 185.1; 514/12–14; 536/27, 23.7; 435/252.3, 69.3

[56] References Cited

U.S. PATENT DOCUMENTS

| | | | |
|---|---|---|---|
| 4,118,469 | 10/1978 | Caldwell et al. | 424/1 |
| 4,427,782 | 1/1984 | Caldwell et al. | 436/542 |
| 4,663,291 | 5/1987 | Rose | 435/259 |
| 5,071,962 | 12/1991 | Morrison et al. | 530/387 |
| 5,075,228 | 12/1991 | Nano et al. | 435/172.3 |

OTHER PUBLICATIONS

Y. Zhang et al. Jan. 1987. J. Immunol. 138(2):575–81. “Protective MAb’s recog . . .”.

H.D. Caldwell, et al. Mar. 1982. Infect. Imm. 35(3):1024–31. “Antigenic Analysis . . .”.

W. Baehr et al, PNAS 85:4000–4, (Jun. 1988) “Mapping antigenic domains expressed by *C. trachomatis* major outer membrane protein genes.”

H.D. Caldwell, et al. Infect. Immun. 35(3):1024–31, (Mar. 1982) “Antigenic analysis of the major outer membrane protein of Chlamydia spp.”

J.W. Conlan, et al, Mol. Microbiol. 2(5):673–79 (1988) “Epitope mapping with solid–phase peptides: identification of type –3 subspecies–species–and genus reactive antibody binding domains on the major outer membrane protein of *Chlamydia trachomatis*”.

R.S. Stephens et al. J. Bacteriol. 169(9):3879–85, (Sep. 1987) “Diversity of *Chlamydia trachomatis* major membrane protein genes.”

*Primary Examiner*—Thomas M. Cunningham
*Attorney, Agent, or Firm*—Knobbe, Martens, Olson & Bear, LLP

[57] ABSTRACT

The nucleotide and deduced amino acid sequences of the four variable domains of the major outer membrane proteins of the 15 serovars of *Chlamydia trachomatis* are disclosed together with sequence and immunogenic analysis of these domains.

20 Claims, 20 Drawing Sheets

A

```
         55         64                     83         92
                    ──────── VDI ────────
B    DVNKEFQMG | -AKPTTTTGNAVAPSTLT-ARE | NPAYGRHMQ
Ba   ......... | -....A.....T......-... | .........
D    ......... | -.....D...SA......-... | .........
E    ......... | -D...S.....T..T...-... | .........
L1   ......... | -....A.....A....C.-... | .........
L2   ......... | -.....A....A....C.-... | .........

F    DVNKEFEMG | EALAGASGNTTSTLSKL-VERT | NPAYGKHMQ
G    ......... | .................-.... | .........

C    DVNKEFQMG | AAPTTSDVAGLQNDPTTNVARP | NPAYGKHMQ
A    ......... | ...........EK..VA..... | .........
H    ......... | .....N.A.D.....K...... | .........
I    ......... | .....K.....E.......... | .........
J    ......... | ...................... | .........
K    ......... | ........E............. | .........
L3   ......... | .E.....T...S.......... | .........
```

B

```
        132      139                    160     166
                 ──────── VDII ────────
B    NLVGLFG | NNENQTKVSNGAFVPNMSLDQS | VVELYT
Ba   ....... | ..........ST.......... | ......
D    ....... | D....KT.KAES-.....F... | ......
E    ....... | D....ST.KTNS-......... | ......
L1   ....... | D....ST.KKD.-.....F... | ......
L2   ....... | D...HAT..DSKL......... | ......

F    NLVGLFG | DGVNATKP-AADSIPNVQLNQS | VVELYT
G    ....... | ..E...Q.-..T.......... | ......

C    NLVGLFG | TKTQSSSFNTAKLIPNTALNEA | VVELYI
A    ....... | ......G.D..NIV......Q. | .....T
H    ....... | ...K..D......V..I...R. | .....T
I    ....... | ......N......V..A...Q. | .....T
J    ....... | ....A......N.F......Q. | .....T
K    ....... | ....Y.K....N.V.....DR. | .....T
L3   ....... | .....TN......V......Q. | .....T
```

C

```
     220    224          237   241
            ─── VDIII ───
B    GYVG | KELPLDLTAGTDAA | TGTK
Ba   .... | ........S..... | ....
D    .... | ..F........... | ....
E    .... | Q.F..A.I...... | ....
L1   .... | ..F........... | ....
L2   .... | Q.F....K....GV | ....

F    GYVG | KEFPLDLTAGTDAA | TGTK
G    .... | Q....A........ | ....

C    GYVG | AEFPLNITAGTEAA | TGTK
A    .... | .....D........ | ....
H    .... | .....D........ | ....
I    .... | .....D.I...... | ....
J    .... | .....D........ | ....
K    .... | V....D........ | ....
L3   .... | .....D........ | ....
```

D

```
     284    288                           317   321
            ──────────── VDIV ────────────
B    AQPK | SAETIFDVTTLNPTIAGAGDVKTSA-EGQLG | DTMC
Ba   .... | .........................-..... | ....
D    .... | ..TA...T...............G.-..... | ....
E    .... | ..TA...T..............A..-..... | ....
L1   .... | L.TA...T...........E..AN.-..... | ....
L2   .... | ..T.V.................A..-..... | ....

F    AQPR | LVTPVVDITTLNPTIAGCGSVAGANTEGQIS | DTMQ
G    ...K | .AK..................VA..S..... | ....

C    AQPK | LAEAILDVTTLNPTIAGKGSVVSAGTDNELA | DTMQ
A    .... | ..KPV..T...........T...SA-E.... | ....
H    .... | ...................T..AS.S..D.. | ....
I    .... | ...................T...SA-E.... | ....
J    .... | ...................T..AS.SE.D.. | ....
K    .... | ...............T...A...S.S..... | ....
L3   .... | ....V.................AS.SE.... | ....
```

FIG. 4

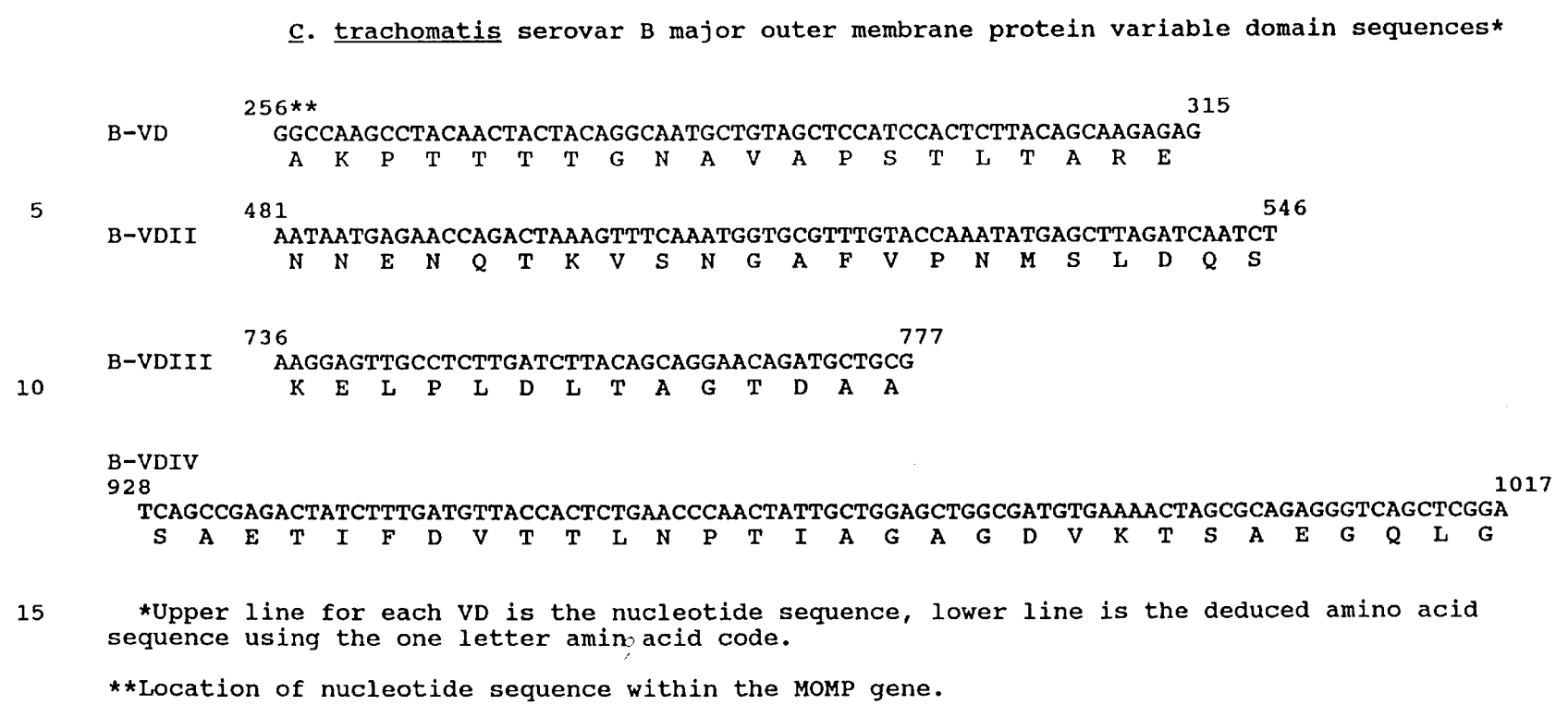

C. trachomatis serovar B major outer membrane protein variable domain sequences*

```
               256**                                                         315
B-VD             GGCCAAGCCTACAACTACTACAGGCAATGCTGTAGCTCCATCCACTCTTACAGCAAGAGAG
                  A  K  P  T  T  T  T  G  N  A  V  A  P  S  T  L  T  A  R  E

               481                                                                 546
B-VDII           AATAATGAGAACCAGACTAAAGTTTCAAATGGTGCGTTTGTACCAAATATGAGCTTAGATCAATCT
                  N  N  E  N  Q  T  K  V  S  N  G  A  F  V  P  N  M  S  L  D  Q  S

               736                                       777
B-VDIII          AAGGAGTTGCCTCTTGATCTTACAGCAGGAACAGATGCTGCG
                  K  E  L  P  L  D  L  T  A  G  T  D  A  A

B-VDIV
928                                                                                         1017
  TCAGCCGAGACTATCTTTGATGTTACCACTCTGAACCCAACTATTGCTGGAGCTGGCGATGTGAAAACTAGCGCAGAGGGTCAGCTCGGA
   S  A  E  T  I  F  D  V  T  T  L  N  P  T  I  A  G  A  G  D  V  K  T  S  A  E  G  Q  L  G
```

*Upper line for each VD is the nucleotide sequence, lower line is the deduced amino acid sequence using the one letter amino acid code.

**Location of nucleotide sequence within the MOMP gene.

*FIG.5*

C. trachomatis serovar Ba major outer membrane protein variable domain sequences*

256** 315
Ba-VDI GCCAAGCCTACAGCTACTACAGGCAATGCTACAGCTCCATCCACTCTTACAGCAAGAGAG
A K P T A T T G N A T A P S T L T A R E 481 546
Ba-VDII AATAATGAGAACCAGACTAAAGTTTCAAATAGTACGTTTGTACCAAATATGAGCTTAGATCAATCT
N N E N Q T K V S N S T F V P N M S L D Q S

Ba-VDIII 736 777
AAGGAGTTGCCTCTTGATCTTACATCAGGAACAGATGCTGCG
K E L P L D L T S G T D A A

Ba-VDIV
928 1017
TCAGCCGAGACTATCTTTGATGTTACCACTCTGAACCCAACTATTGCTGGAGCTGGCGATGTGAAAACTAGCGCAGAGGGTCAGCTCGGA
S A E T I F D V T T L N P T I A G A G D V K T S A E G Q L G

*Upper line for each VD is the nucleotide sequence, lower line is the deduced amino acid sequence using the one letter amino acid code.

**Location of nucleotide sequence within the MOMP gene.

*FIG. 6*

<u>C</u>. <u>trachomatis</u> serovar D major outer membrane protein variable domain sequences*

```
          256**                                                          315
D-VDI       GCCAAGCCTACAACTGATACAGGCAATAGTGCAGCTCCATCCACTCTTACAGCAAGAGAG
             A  K  P  T  T  D  T  G  N  S  A  A  P  S  T  L  T  A  R  E

          481                                                              543
D-VDII      GATAATGAAAATCAAAAAACGGTCAAAGCGGAGTCTGTACCAAATATGAGCTTTGATCAATCT
             D  N  E  N  Q  K  T  V  K  A  E  S  V  P  N  M  S  F  D  Q  S

          733                                      744
D-VDIII     AAGGAGTTTCCTCTTGATCTTACAGCAGGAACAGATGCTGCG
             K  E  F  P  L  D  L  T  A  G  T  D  A  A

D-VDIV      925
1014
  TCAGCTACAGCTATTTTTGATACTACCACGCTTAACCCAACTATTGCTGGAGCTGGCGATGTGAAAACTGGCGCAGAGGGTCAGCTCGGA
   S  A  T  A  I  F  D  T  T  T  L  N  P  T  I  A  G  A  G  D  V  K  T  G  A  E  G  Q  L  G
```

*Upper line for each VD is the nucleotide sequence, lower line is the deduced amino acid sequence using the one letter amino acid code.

**Location of nucleotide sequence within the MOMP gene.

*FIG. 7*

C. trachomatis serovar E major outer membrane protein variable domain sequences*

```
     256**                                                  315
E-VDI   GACAAGCCTACAAGTACTACAGGCAATGCTACAGCTCCAACCACTCTTACAGCAAGAGAG
         D  K  P  T  S  T  T  G  N  A  T  A  P  T  T  L  T  A  R  E

     481                                                       543
E-VDII GATAATGAAAATCAAAGCACGGTCAAAACGAATTCTGTACCAAATATGAGCTTAGATCAATCT
         D  N  E  N  Q  S  T  V  K  T  N  S  V  P  N  M  S  L  D  Q  S

          733                                       744
E-VDIII     CAAGAATTCCCTCTTGCACTCATAGCAGGAACTGATGCAGCG
             Q  E  F  P  L  A  L  I  A  G  T  D  A  A

E-VDIV
925                                                                                   1014
  TCAGCTACAGCTATCTTTGATACTACCACGCTTAACCCAACTATTGCTGGAGCTGGCGATGTGAAAGCTACGCAGAGGGTCAGCTCGGA
   S  A  T  A  I  F  D  T  T  T  L  N  P  T  I  A  G  A  G  D  V  K  A  S  A  E  G  Q  LG
```

*Upper line for each VD is the nucleotide sequence, lower line is the deduced amino acid sequence using the one letter amino acid code.

**Location of nucleotide sequence within the MOMP gene.

*FIG. 8*

C. trachomatis serovar L1 major outer membrane protein variable domain sequences*

```
            256**                                                     315
L1-VDI        GCCAAGCCTACAGCTACTACAGGCAATGCTGCAGCTCCATCCACTTGTACAGCAAGAGAG
               A  K  P  T  A  T  T  G  N  A  A  A  P  S  T  C  T  A  R  E

            481                                                          543
L1-VDII       GATAATGAAAATCAAAGCACGGTCAAAAAGGATGCTGTACCAAATATGAGCTTTGATCAATCT
               D  N  E  N  Q  S  T  V  K  K  D  A  V  P  N  M  S  F  D  Q  S

            733                                       774
L1-VDIII      AAGGAGTTTCCTCTTGATCTTACAGCAGGAACAGATGCTGCG
               K  E  F  P  L  D  L  T  A  G  T  D  A  A

L1-VDIV
925                                                                                        1014
  TTAGCTACAGCTATCTTTGATACTACCACGCTTAACCCAACTATTGCTGGAGCTGGCGAGGTGAAAGCTAACGCAGAGGGTCAGCTCGGA
   L  A  T  A  I  F  D  T  T  T  L  N  P  T  I  A  G  A  G  E  V  K  A  N  A  E  G  Q  L  G
```

*Upper line for each VD is the nucleotide sequence, lower line is the deduced amino acid sequence using the one letter amino acid code.

**Location of nucleotide sequence within the MOMP gene.

FIG.9

<u>C</u>. <u>trachomatis</u> serovar L2 major outer membrane protein variable domain sequences*

```
            256**                                                       315
L2-VDI       GCCAAGCCTACAACTGCTACAGGCAATGCTGCAGCTCCATCCACTTGTACAGCAAGAGAG
              A  K  P  T  T  A  T  G  N  A  A  A  P  S  T  C  T  A  R  E

            481                                                               546
L2-VDII      GATAATGAGAACCATGCTACAGTTTCAGATAGTAAGCTTGTACCAAATATGAGCTTAGATCAATCT
              D  N  E  N  H  A  T  V  S  D  S  K  L  V  P  N  M  S  L  D  Q  S

            736                                       777
L2-VDIII     CAAGAATTCCCTCTTGATCTTAAAGCAGGAACAGATGGTGTG
              Q  E  F  P  L  D  L  K  A  G  T  D  G  V

L2-VDIV
928                                                                                          1017
 TCAGCTACAACTGTCTTTGATGTTACCACTCTGAACCCAACTATTGCTGGAGCTGGCGATGTGAAAGCTAGCGCAGAGGGTCAGCTCGGA
  S  A  T  T  V  F  D  V  T  T  L  N  P  T  I  A  G  A  G  D  V  K  A  S  A  E  G  Q  L  G
```

*Upper line for each VD is the nucleotide sequence, lower line is the deduced amino acid sequence using the one letter amino acid code.

**Location of nucleotide sequence within the MOMP gene.

*FIG. 10*

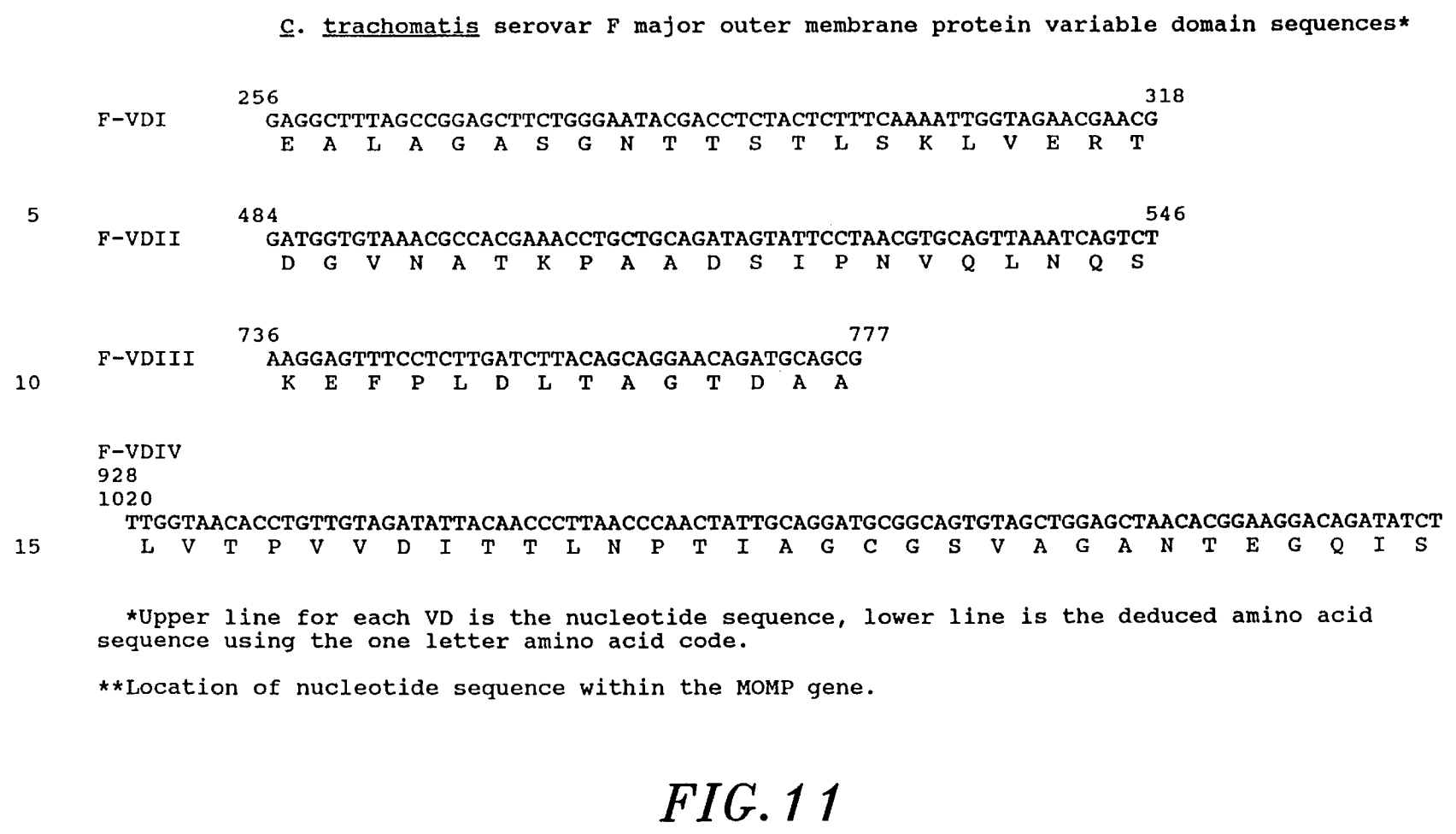

C. trachomatis serovar F major outer membrane protein variable domain sequences*

```
          256                                                          318
F-VDI       GAGGCTTTAGCCGGAGCTTCTGGGAATACGACCTCTACTCTTTCAAAATTGGTAGAACGAACG
             E  A  L  A  G  A  S  G  N  T  T  S  T  L  S  K  L  V  E  R  T

          484                                                          546
F-VDII      GATGGTGTAAACGCCACGAAACCTGCTGCAGATAGTATTCCTAACGTGCAGTTAAATCAGTCT
             D  G  V  N  A  T  K  P  A  A  D  S  I  P  N  V  Q  L  N  Q  S

          736                                      777
F-VDIII     AAGGAGTTTCCTCTTGATCTTACAGCAGGAACAGATGCAGCG
             K  E  F  P  L  D  L  T  A  G  T  D  A  A

F-VDIV
928
1020
  TTGGTAACACCTGTTGTAGATATTACAACCCTTAACCCAACTATTGCAGGATGCGGCAGTGTAGCTGGAGCTAACACGGAAGGACAGATATCT
   L  V  T  P  V  V  D  I  T  T  L  N  P  T  I  A  G  C  G  S  V  A  G  A  N  T  E  G  Q  I  S
```

*Upper line for each VD is the nucleotide sequence, lower line is the deduced amino acid sequence using the one letter amino acid code.

**Location of nucleotide sequence within the MOMP gene.

FIG. 11

<u>C</u>. <u>trachomatis</u> serovar G majar outer membrane protein variable domain sequences*

```
              256**                                                    318
G-VDI           GAGGCTTTAGCCGGAGCTTCTGGGAATACGACCTCTACTCTTTCAAAATTGGTAGAACGAACG
                 E  A  L  A  G  A  S  G  N  T  T  S  T  L  S  K  L  V  E  R  T

              484                                                      546
G-VDII          GATGGTGAAAACGCCACGCAGCCTGCTGCAACAAGTATTCCTAACGTGCAGTTAAATCAGTCT
                 D  G  E  N  A  T  Q  P  A  A  T  S  I  P  N  V  Q  L  N  Q  S

              736                                   777
G-VDIII         CAAGAATTCCCTCTTGCACTCACAGCAGGAACTGATGCAGCG
                 Q  E  F  P  L  A  L  T  A  G  T  D  A  A

G-VDIV
928                                                                                          1020
  TTGGCAAAACCTGTTGTAGATATTACAACCCTTAACCCAACTATTGCAGGATGCGGCAGTGTAGCTGCAGCTAACTCGGAAGGACAGATATCT
   L  A  K  P  V  V  D  I  T  T  L  N  P  T  I  A  G  C  G  S  V  V  A  A  N  S  E  G  Q  I  S
```

*Upper line for each VD is the nucleotide sequence, lower line is the deduced amino acid sequence using the one letter amino acid code.

**Location of nucleotide sequence within the MOMP gene.

FIG. 12

<u>C</u>. <u>trachomatis</u> serovar C major outer membrane protein variable domain sequences*

```
            256**                                                             321
C-VDI        GCGGCGCCTACTACCAGCGATGTAGCAGGCTTACAAAACGATCCAACAACAAACGTTGCTCGTCCA
              A  A  P  T  T  S  D  V  A  G  L  Q  N  D  P  T  T  N  V  A  R  P

            487                                                               552
C-VDII       ACAAAAACACAATCTTCTAGCTTTAATACAGCGAATATTATTCCTAACACTGCTTTGAATGAAGCT
              T  K  T  Q  S  S  S  F  N  T  A  K  L  I  P  N  T  A  L  N  E  A

C-VDIII     742                                     783
             GCGGAATTTCCACTTAATATTACCGCAGGAACAGAAGCTGCG
              A  E  F  P  L  N  I  T  A  G  T  E  A  A

C-VDIV
934                                                                                         1026
  TTGGCTGAAGCAATCTTGGATGTCACTACTCTGAACCCGACTATCGCTGGTAAAGGAAGTGTGGTCTCTGCCGGAACCGATAACGAACTGGCT
   L  A  E  A  I  L  D  V  T  T  L  N  P  T  I  A  G  K  G  S  V  V  S  A  G  T  D  N  E  L  A
```

*Upper line for each VD is the nucleotide sequence, lower line is the deduced amino acid sequence using the one letter amino acid code.

**Location of nucleotide sequence within the MOMP gene.

FIG. 13

_C_. _trachomatis_ serovar A major outer membrane protein variable domain sequences*

```
          256*                                                              321
A-VDI       GCGGCGCCTACTACCAGCGATGTAGCAGGCTTAGAAAACGATCCAGTAGCAAATGTTGCTCGCCCA
             A  A  P  T  T  S  D  V  A  G  L  E  K  D  P  V  A  N  V  A  R  P

          487                                                               552
A-VDII      ACAAAAACACAATCTTCTGGCTTTGATACAGCGAATATTGTTCCTAACACTGCTTTGAATCAAGCT
             T  K  T  Q  S  S  G  F  D  T  A  N  I  V  P  N  T  A  L  N  Q  A

          742                                       783
A-VDIII     GCGGAATTTCCACTTGATATTACCGCAGGAACAGAAGCTGCG
             A  E  F  P  L  D  I  T  A  G  T  E  A  A

A-VDIV
934                                                                                     1023
 TTGGCTAAACCAGTCTTGGATACCACTACTCTAAACCCGACCATCGCTGGTAAAGGAACTGTGGTCTCTTCCGCAGAAAACGAACTGGCT
  L  A  K  P  V  L  D  T  T  T  L  N  P  T  I  A  G  K  G  T  V  V  S  S  A  E  N  E  L  A
```

*Upper line for each VD is the nucleotide sequence, lower line is the deduced amino acid sequence using the one letter amino acid code.

**Location of nucleotide sequence within the MOMP gene.

FIG. 14

C. trachomatis serovar H major outer membrane protein variable domain sequences*

```
            256**                                                     321
H-VDI        GCGGCGCCTACTACCAACGATGCAGCAGACTTACAAAACGATCCAAAAACAAATGTTGCTCGTCCA
              A  A  P  T  T  N  D  A  A  D  L  Q  N  D  P  K  T  N  V  A  R  P

            487                                                       552
H-VDII       ACAAAAACAAAATCTTCTGATTTTAATACAGCGAAGCTTGTTCCTAACATTGCTTTGAATCGAGCT
              T  K  T  K  S  S  D  F  N  T  A  K  L  V  P  N  I  A  L  N  R  A

            742                                       783
H-VDIII      GCGGAATTTCCACTTGATATTACCGCAGGAACAGAAGCTGCG
              A  E  F  P  L  D  I  T  A  G  T  E  A  A

H-VDIV
934                                                                                              1026
  TTGGCTGAAGCAATCTTGGATGTCACTACTCTAAACCCGACCATCGCTGGTAAAGGAACTGTGGTCGCTTCCGGAAGCGATAACGACCTGGCT
   L  A  E  A  I  L  D  V  T  T  L  N  P  T  I  A  G  K  G  T  V  V  A  S  G  S  D  N  D  L  A
```

*Upper line for each VD is the nucleotide sequence, lower line is the deduced amino acid sequence using the one letter amino acid code.

**Location of nucleotide sequence within the MOMP gene.

*FIG. 15*

_C._ _trachomatis_ serovar I major outer membrane protein variable domain sequences*

```
          256**                                                            321
I-VDI       GCGGCGCCTACTACCAAGGATGTAGCAGGCTTAGAAAACGATCCAACAACAAATGTTGCTCGTCCA
             A  A  P  T  T  K  D  V  A  G  L  E  N  D  P  T  T  N  V  A  R  P

          487                                                              552
I-VDII      ACAAAAACACAATCTTCTAACTTTAATACAGCGAAGCTTGTTCCTAACGCTGCTTTGAATCAAGCT
             T  K  T  Q  S  S  N  F  N  T  A  K  L  V  P  N  A  A  L  N  Q  A

          742                                      783
I-VDIII     GCGGAATTTCCACTTGATATTATCGCAGGAACAGAAGCTGCG
             A  E  F  P  L  D  I  I  A  G  T  E  A  A

I-VDIV
934                                                                                        1023
  TTGGCTGAAGCAATCTTGGATGTCACTACTCTAAACCCGACCATCGCTGGTAAAGGAACTGTGGTCTCTTCCGCAGAAAACGAACTGGCT
   L  A  E  A  I  L  D  V  T  T  L  N  P  T  I  A  G  K  G  T  V  V  S  S  A  E  N  E  L  A
```

*Upper line for each VD is the nucleotide sequence, lower line is the deduced amino acid sequence using the one letter amino acid code.

**Location of nucleotide sequence within the MOMP gene.

FIG. 16

C. trachomatis serovar J major outer membrane protein variable domain sequences*

```
           256**                                                               321
J-VDI        GCGGCGCCTACTACCAGCGATGTAGCAGGCTTACAAAACGATCCAACAACAAATGTTGCTCGTCCA
              A  A  P  T  T  S  D  V  A  G  L  Q  N  D  P  T  T  N  V  A  R  P

           487                                                                 552
J-VDII       ACAAAAACACAAGCTTCTAGCTTTAATACAGCGAATCTTTTTCCTAACACTGCTTTGAATCAAGCT
              T  K  T  Q  A  S  S  F  N  T  A  N  L  F  P  N  T  A  L  N  Q  A

           742                                       783
J-VDIII      GCGGAATTTCCACTTGATATTACCGCAGGAACAGAAGCTGCG
              A  E  F  P  L  D  I  T  A  G  T  E  A  A

J-VDIV
934                                                                                              1026
  TTGGCTGAAGCAATCTTGGATGTCACTACTCTAAACCCGACCATCGCTGGTAAAGGAACTGTGGTCGCTTCCGGAAGCGAAAACGACCTGGCT
   L  A  E  A  I  L  D  V  T  T  L  N  P  T  I  A  G  K  G  T  V  V  A  S  G  S  E  N  D  L  A
```

*Upper line for each VD is the nucleotide sequence, lower line is the deduced amino acid sequence using the one letter amino acid code.

**Location of nucleotide sequence within the MOMP gene.

FIG. 17

C. trachomatis serovar K major outer membrane protein variable domain sequences*

```
              256**                                                         321
K-VDI          GCGGCGCCTACTACCAGCGATGTAGAAGGCTTACAAAACGATCCAACAACAAATGTTGCTCGTCCA
                A  A  P  T  T  S  D  V  E  G  L  Q  N  D  P  T  T  N  V  A  R  P

              487                                                           552
K-VDII         ACAAAAACACAATATTCTAAGTTTAATACAGCGAATCTTGTTCCTAACACTGCTTTGGATCGAGCT
                T  K  T  Q  Y  S  K  F  N  T  A  N  L  V  P  N  T  A  L  D  R  A

              742                                        783
K-VDIII        GTGGAATTTCCACTTGATATTACCGCAGGAACAGAAGCTGCG
                V  E  F  P  L  D  I  T  A  G  T  E  A  A

K-VDIV
934                                                                                         1026
  TTGGCTGAAGCAATCTTGGATGTCACTACTCTAAACCCGACCATCACTGGTAAAGGAGCTGTGGTCTCTTCCGGAAGCGATAACGAACTGGCT
   L  A  E  A  I  L  D  V  T  T  L  N  P  T  I  T  G  K  G  A  V  V  S  S  G  S  D  N  E  L  A
```

*Upper line for each VD is the nucleotide sequence, lower line is the deduced amino acid sequence using the one letter amino acid code.

**Location of nucleotide sequence within the MOMP gene.

FIG. 18

C. *trachomatis* serovar L3 major outer membrane protein variable domain sequences*

L3-VDI 256** ... 321
GCCGAGCCTACTACCAGCGATACAGCGGGCTTATCAAACGATCCAACAACAAATGTTGCTCGTCCA
A E P T T S D T A G L S N D P T T N V A R P

L3-VDII 487 ... 552
ACAAAAACACAATCTACTAACTTTAATACAGCGAAGCTTGTTCCTAACACTGCTTTGAATCAAGCT
T K T Q S T N F N T A K L V P N T A L N Q A

L3-VDIII 742 ... 783
GCGGAATTTCCACTTGATATTACCGCAGGAACAGAAGCTGCG
A E F P L D I T A G T E A A

L3-VDIV
934 ... 1026
TTGGCTGAAGCAGTCTTGGATGTCACTACTCTAAACCCGACCATCGCTGGTAAAGGAAGTGTGGTCGCTTCCGGCAGCGAAAACGAACTGGCT
L A E A V L D V T T L N P T I A G K G S V V A S G S E N E L A

*Upper line for each VD is the nucleotide sequence, lower line is the deduced amino acid sequence using the one letter amino acid code.

**Location of nucleotide sequence within the MOMP gene.

*FIG. 19*

NUCLEOTIDE AND AMINO ACID SEQUENCES OF THE FOUR VARIABLE DOMAINS OF THE MAJOR OUTER MEMBRANE PROTEINS OF *CHLAMYDIA TRACHOMATIS*

This is a continuation of application Ser. No. 07/324,664, filed on Mar. 17, 1989, which is now abandoned.

BACKGROUND OF THE INVENTION

In the United States, urogenital infections with *Chlamydia trachomatis* are the leading sexually transmitted disease with an estimated 10 million new cases reported each year. The urogenital infections result in involuntary infertility in 100–200,000 women each year. It is estimated that equal or greater numbers of these infections occur in European countries. In addition, ocular infection with *C. trachomatis* results in blinding trachoma which afflicts approximately 500 million individuals from developing countries. Improved diagnostic methodologies and vaccines or immunoprophylactic preventative measures are needed to manage and control the disease.

*Chlamydia trachomatis* isolates occur as 15 distinct serovars. Based on serological relatedness, these 15 serovars have been divided into three serogroups; B serogroup (serovars B, Ba, D, E, L1 and L2), intermediate serogroup (serovars F, G, K and L3), and C serogroup (serovars A, C, H, I and J). The antigen that confers serovar and serogroup-specificities to chlamydia is the major outer membrane protein (MOMP), and protective immunity developed during chlamydial ocular infection is thought to be directed at serovar and serogroup MOMP determinants.

The genes encoding the MOMP of the *C. trachomatis* serovars A, B, C, L1 and L2 have been cloned and sequenced (Pickett et al., FEMS Microbiol. Lett. 42:185–190 (1987); Stephen et al., J. Bacteriol. 168:1277–1282 (1986); and Stephens et al., J. Bacteriol 169:3879–3885 (1987); Baehr et al., Proc. Natl. Acad. Sci. USA, 85:4000–4004 (1988)). Comparative analysis of their amino acid sequences show the MOMP genes to be highly conserved structures that contain four evenly spaced domains whose sequences vary among the different serovars. The locations of these nucleotide and amino acid sequence variable domains (VDs) are:

VDI—nucleotides 256–315 and residues 64–83;

VDII—nucleotides 481–546 and residues 139–160;

VDIII—nucleotides 736–777 and residues 224–237;

VDIV–nucleotides 928–1017 and residues 288–317.

Epitope mapping has shown that three of the four VD domains (I, II and IV) contain contiguous antigenic determinants which elicit the formation of serovar, subspecies (determinants common to three or more serovars within a serogroup), serogroup or species-specific antibodies.

Variable domains I and II, which demonstrate the greatest amount of inter serogroup sequence variation, are the locations of the serovar-specific determinants. Variable domain IV is the largest of the MOMP VDs and is located near the C-terminus of the protein. VDIV is the location of subspecies and serogroup antigenic determinants, as well as a highly conserved species-specific antigenic determinant. Antigenic determinants have not been mapped to VDIII, the smallest and least variable domain of the MOMP genes.

Variable domains I, II and IV of the MOMP of *C. trachomatis* protrude from the cell surface towards the external environment as demonstrated by their susceptibility to cleavage by trypsin, and their accessibility to antibody binding. Trypsin cleavage in both VDII and VDIV, but not within VDIV alone, decreases chlamydial attachment to HeLa cells suggesting that these domains, or conformational MOMP structures that are dependent on the integrity of these domains, may function as a chlamydial ligand.

Based on the immunological and biological relationships among MOMP VD structure and function, and the fact that the MOMP VDs appear to be the major variable sequences between serovars, the present inventors sought to identify the nucleotide and amino acid sequences of the MOMP VDs I–IV of *C. trachomatis* serovars Ba, D, E, F, G, H, I, J, K and L3, and to confirm those of serovars B, A, C, L1 and L2.

SUMMARY OF THE INVENTION

The amino acid sequences of the major outer membrane protein genes from *Chlamydia trachomatis* serovars A, B, C, L1 and L2 have been shown to be conserved with the exception of four variable domains in which major neutralizing and serotyping antigenic determinants have been located. Using oligonucleotide primer extension sequencing of MOMP mRNA, the nucleotide sequences of the four MOMP VDs of the remaining 10 *C. trachomatis* serovars were determined by the present inventors and the amino acid sequences deduced therefrom. The sequencing technique was rapid and required minimal amounts of total RNA, i.e., only 35 $\mu$g of RNA from chlamydial infected HeLa cells was needed to sequence all 4 variable domains for a given serovar. Use of the disclosed technique also circumvented the more standard and laborious approach of molecular cloning and direct DNA sequencing which had been employed in the past to determine the sequences of the MOMP gene to serovars A, B, C, L1 and L2.

As noted above, the nucleotide sequences were employed to deduce the corresponding amino acid sequences. Comparative analysis of the amino acid sequence homology of the four variable domains permitted the present inventors to separate the fifteen serovars into three serogroups:

Group 1—serovars B, Ba, D, E, L1 and L2;

Group 2—serovars G and F;

Group 3—serovars A, C, H, I, J, K and L3.

The four variable domains were also analyzed for immunogenicity based on the hydrophilicity and charge values of each domain (Baehr et al., supra). The MOMP VDs with the greatest total hydrophilicity and charge values were found to be the locations of the antigenic determinants recognized by MOMP specific monoclonal antibodies (Stephens et al., supra; Baehr et al., supra).

The nucleotide, amino acid sequences and hydrophilicity/charge value analyses are advantageous because they will assist in the selection of appropriate MOMP antigenic determinants to be used in the construction of synthetic peptides, subunits or recombinant chlamydial vaccines. Examples of such recombinant vaccines include infectious enteric vectors (avirulent *Salmonella typhimurium* and/or Sabin Type I polio virus) expressing MOMP variable domain sequences as antigenic chimeras or hybrid molecules.

The present invention will allow the production of reagents and methodologies applicable in the development of new diagnostic tests for *C. trachomatis* infections and serological tests for serotyping. Specifically, species or sero-type specific oligopeptides conjugated to an array of reporter or detector groups could be used in various conventional non-immunologic assays including standard hybridization techniques.

Likewise, reagents for use in immunologic or serologic tests could be prepared based on the sequences presently disclosed; the conserved VD-IV peptide sequence TTLNT- TIAG would permit species specific identification, while the non-conserved sequences would enable one to make serotype specific identification. It is contemplated by the present inventors that such reagents would be suitable for use in standard immunologic procedures such as ELISA and radioimmunoassay techniques.

The invention will be more fully described in the detailed description and drawings which follow.

DESCRIPTION OF THE DRAWINGS

FIG. 4. (A, B, C and D) The deduced amino acid sequences of the MOMP VDs 1, 2, 3 and 4, respectively, of the 15 *C. trachomatis* serovars. The boxed regions of the sequences identity each of the four VDs. Serovars B, F and C MOMP amino acid sequences were used as prototypes for comparative sequence analysis.

FIG. 5. *C. trachomatis* serovar B MOMP variable domain sequence.

FIG. 6. *C. trachomatis* serovar Ba MOMP variable domain sequence.

FIG. 7. *C. trachomatis* serovar D MOMP variable domain sequence.

FIG. 8. *C. trachomatis* serovar E MOMP variable domain sequence.

FIG. 9. *C. trachomatis* serovar L1 MOMP variable domain sequence.

FIG. 10. *C. trachomatis* serovar L2 MOMP variable domain sequence.

FIG. 11. *C. trachomatis* serovar F MOMP variable domain sequence.

FIG. 12. *C. trachomatis* serovar G MOMP variable domain sequence.

FIG. 13. *C. trachomatis* serovar C MOMP variable domain sequence.

FIG. 14. *C. trachomatis* serovar A MOMP variable domain sequence.

FIG. 15. *C. trachomatis* serovar H MOMP variable domain sequence.

FIG. 16. *C. trachomatis* serovar I MOMP variable domain sequence.

FIG. 17. *C. trachomatis* serovar J MOMP variable domain sequence.

FIG. 18. *C. trachomatis* serovar K MOMP variable domain sequence.

FIG. 19. *C. trachomatis* serovar L3 MOMP variable domain sequence.

DETAILED DESCRIPTION OF THE INVENTION

All references cited below are specifically incorporated into the specification by reference.

I. MATERIALS AND METHODS

A. Chlamydiae

*C. trachomatis* serovars: A/Har-13, B/TW-5/OT, Ba/AP-2, C/TW-3/OT, D/UW-3/Cx, E/Bour, F/IC-Cal-13, G/UW-57/Cx, H/UW-4/Cx, I/UW-12/Ur, J/UW-36/Cx, K/UW-31/Cx, LGV/L1-440, LGV/L2-434 and LGV/L3-404 were employed herein and were immunotyped by the micro-immunofluorescence (micro-IF) procedure of Wang et al. (J. Infect. Dis. 152:791–800 (1985)). Serovars A, E and F were obtained from the American Type Culture Collection (ATCC, Rockville, Md.). All other serovars were obtained from Dr. Cho-Chou Kuo, Department of Pathobiology, University of Washington, Seattle, Wash.

B. RNA Extraction

Approximately $2\times10^8$ HeLa 229 cells grown in stationary culture were each infected with one chlamydial serovar. Infected HeLa cells were removed from the culture flasks with trypsin 24-hours post-infection for serovars L1, L2 and L3, and 36-hours post-infection for all other serovars. Cell suspensions were then pooled, centrifuged and washed twice in cold (4° C.) phosphate-buffered saline (PBS), 0.02M sodium phosphate, 0.15M NaCl, pH 7.2. Cells were lysed in 5 ml of cold guanidine isothiocyanate lysis buffer (Current Protocols in Molecular Biology, Wiley Inter Science, p. 4.2.4 (1987)). The resulting suspension was then gently refluxed through an 18 gauge needle 15–20 times to shear the DNA.

Total RNA was extracted (2×) from the solution using hot acidic phenol (65° C., pH 5.0), followed by two extractions with chloroform/isoamyl alcohol (24:1 vol/vol). The RNA from each pool was precipitated with two volumes of cold ethanol (−20° C.). The precipitate was evaporated to dryness using a Speed-vac (Bachofer, Reutlingen, FGR). The RNAs were resuspended in glass distilled water at a concentration of 20–40 μg/ml and stored at −70° C.

C. Synthetic Oligonucleotides

Oligonucleotides (21 mers) complementary to the + strand MOMP DNAs flanking the 3' end of each VD were synthesized using a SAM1 automated synthesis instrument (Biosearch, San Rafael, Calif.) by the N-methylimidazole phosphotriester method described by Grayston et al. (J. Infect. Dis. 132:87–104 (1975)) and according to the manufacturer's instructions. De-blocked oligonucleotides were evaporated to dryness using a Speed-Vac, and were then dissolved in distilled water at a concentration of 10–30 mg/ml and stored at −20° C. Oligonucleotides were constructed according to the published sequences of the A, B, C, and L2 MOMP gene serovars (Stephens et al., J. Bacteriol.

168, supra and Baehr et al., supra), as well as the unpublished F serovar sequence which was determined by the present inventors.

Figure 1:
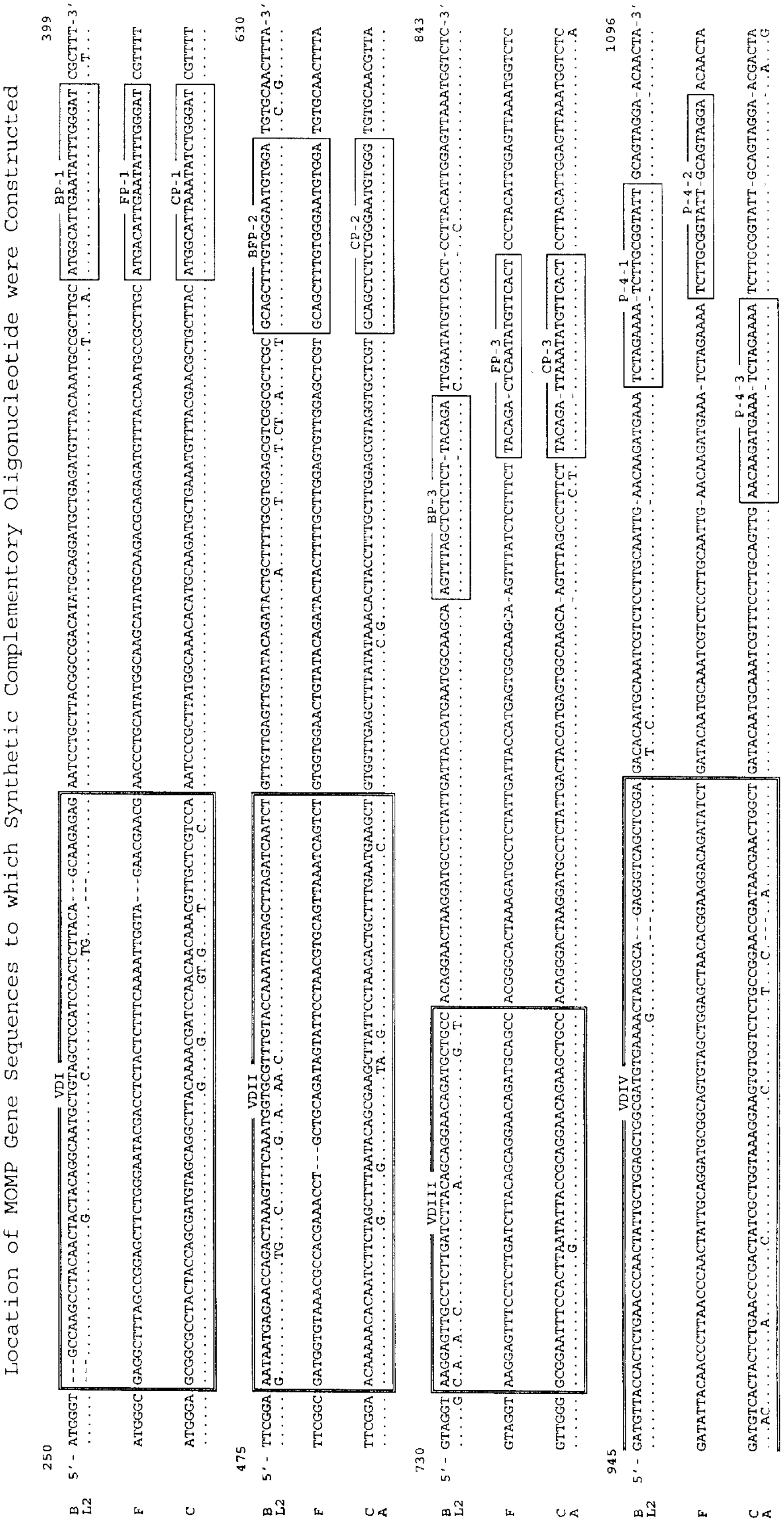
FIG. 1. Location of the MOMP gene sequences to which synthetic complementary oligonucleotides were constructed and used for primer extension mRNA sequencing of MOMP VDs. The MOMP gene sequences identified by single lined boxes are those to which synthetic oligonucleotides were constructed. The double lined boxes identify the four variable domain regions of B, L2, A, C, and F MOMP genes.

The MOMP gene sequences to which synthetic complementary oligonucleotides were constructed, and their location in the MOMP genes are shown in FIG. 1. The oligonucleotide number, its sequence, and the MOMP serovar and VD for which the oligonucleotide was used for primer extension mRNA sequencing are summarized below in Table I.

TABLE 1

Oligonucleotides Used in Primer-extension mRNA Sequencing of *C. trachomatis* MOMP VDs

| Oligonucleotide number | Oligonucleotide sequence | Serovars and their VDS sequencing with oligonucleotide primers |
|---|---|---|
| BP-1 | 5'-ATCCCAAATATTCAATGCCAT-3' | VDIs of B,Ba,D,E,G,L1,L2 |
| CP-1 | ATCCCAGATATTTAATGCCAT | VDIs of A,C,H,I,J,K,L3 |
| FP-1 | ATCCAAATATTCAATGTCAT | VDIs of F,G |
| BFP-2 | TCCACATTCCCACAAAGCTGC | VDIIs of B,Ba,D,E,F,G,L1,L2 |
| CP-2 | CCCACATTCCCAGAGAGCTGC | VDIIs of A,C,H,I,J,K,L3 |
| BP-3 | TCTGTAAGAGAGAGCTAAACT | VDIIIs of B,Ba,D,E,L1,L2 |
| CP-3 | AGTGAACATATTTAATCTGTA | VDIIIs of A,C,H,I,J,K,L3 |
| FP-3 | AGTGAACATATTGAGTCTGTA | VDIIIs of F,G |
| P-4-1 | AATACCGCAAGATTTTCTAGA | VDIVs of A,B,Ba,C,D,E,F,H,I, J,K,L1,L2 |
| P-4-2 | TCCTACTGCAATACCGCAAGA | VDIVS of L3,G, (ND*) |
| P-4-3 | TTTTCTAGATTTCATCTTGTT | VDIV of J, (ND*) |

D. Primer Extension and DNA Seqencing

The dideoxynucleotide chain terminating method of Sanger et al. (Proc. Natl. Acad. Sci. USA 74:5463–5467 (1977) modified for the use with reverse transcriptase and RNA templates as described by Lane et al. (Proc. Natl. Acad. Sci. USA 82:6955–6959 (1985)) was used for sequence determinations. In summary, oligonucleotides were 5' end labeled with [$^{32}$P]dATP (3,000 Ci/mmol—New England Nuclear, Boston, Mass.) using T4 polynucleotide kinase (10,000 U/ml—New England Biolabs, Beverly, Mass.) as described by Maniatis et al. in *A laboratory manual.*pp. 1–545 (Cold Spring Harbor Laboratory, Cold Spring Harbor, N.Y. (1982). Labeled oligonucleotides were isolated on Sephadex G-25 columns (Boehringer Mannheim Biochemicals, Indianapolis, Ind.). The oligonucleotide primers were then hybridized to MOMP mRNA templates in 12.5 $\mu$l reaction mixtures containing 2.5 $\mu$l 5× annealing buffer (250 mM Tris-HCl, 300 mM NaCl, 250 mM DTT, and 5 mM EDTA, pH 8.3), 7.5 $\mu$l of total RNA (3–10 $\mu$g/$\mu$l), and 2.5 $\mu$l of kinased primer (2–2.5 $\mu$M).

The mixtures were heated at 90° C. for 3 minutes, centrifuged and then allowed to cool slowly to 45° C. over a 30 minute period. 2 $\mu$l of the hybridized mixture was then added to each of four tubes containing 3 $\mu$l of reaction mixture (250 mM Tris-HCl, pH 8.3, 300 mM NaCl, 50 mM DTT, 30 mM $MgCl_2$, 2 mM dNTPs, 0.4 mM ddNTPs and 0.6–0.8 U/$\mu$l avian myeloblastosis virus reverse transcriptase (20,000 U/ml—Pharmacia Fine Chemicals, Inc., Piscataway, N.J.)). The mixtures were incubated at 45° C. for 40 minutes then the reactions were stopped by evaporating the tubes to dryness in a Speed-vac. Following evaporation, the samples were resuspended in 3 $\mu$l of 100% formamide containing 0.8% xylene cyanol and 0.8% bromophenol blue and heated at 95° C. for 3 minutes. The samples were then promptly loaded on sequencing gels (8% polyacrylamide) to achieve separation. Following separation the gels were fixed with methanol, dried then autoradiographed.

II. Sequence Analysis

A. Primer Extension and DNA Sequencing

Figure 2:
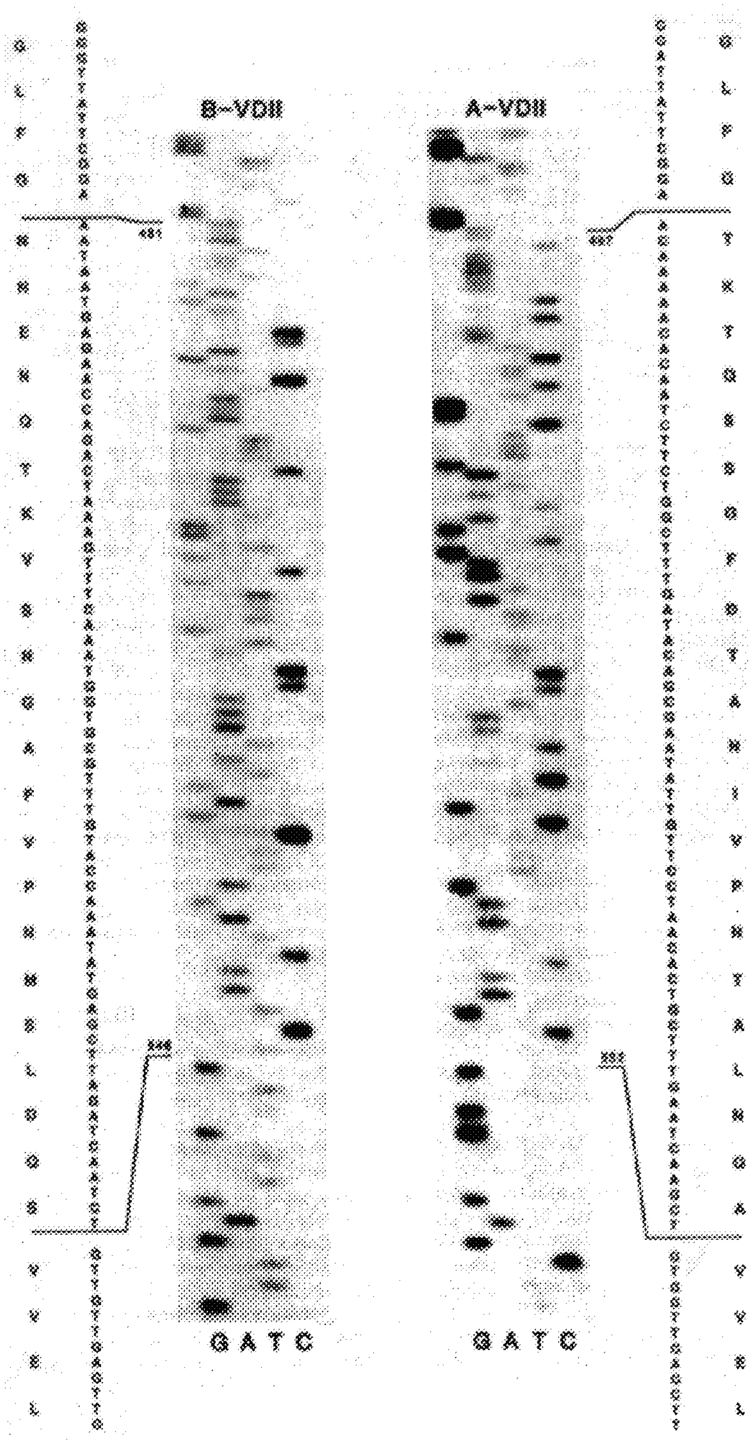
FIG. 2. Sequencing of serovar B and A MOMP VDII by primer extension of MOMP mRNA. Total RNA was isolated from HeLa 229 cells infected with serovars B and A and annealed to kinased oligonucleotides BFP-2 and CP-2 (Table 1), respectively. The oligonucleotides were complementary to the non-coding strand of MOMP gene sequences 50 nucleotides downstream 3' of VDII. The RNA templates were transcribed with reverse transcriptase, and the sequences of the transcribed DNAs determined by the dideoxynucleotide chain termination method. Audioradiographs were read to depict+strand MOMP DNA sequences. The nucleotide numbers shown for each MOMP are the beginning and end of the sequence encoding VDII of each protein. The results shown are representative of sequencing results obtained for all other serovars' VDs.

Using the oligonucleotide primers described above, the VD-encoding portions of the MOMPs mRNA were sequenced. A representative sequencing gel is shown in FIG. 2 wherein MOMP B-VDII and A-VDII are shown. Oligonucleotides BFP-2 and CP-2 were employed in this sequencing as primers. The mRNA derived MOMP sequences depicted are identical to the previously published genomic DNA sequences for the MOMP B-VDII and A-VDII (Stephens et al., supra and Baehr et al., supra), thereby demonstrating both the feasibility and accuracy of this sequencing method.

B. Sequence Analysis

Figure 3A:
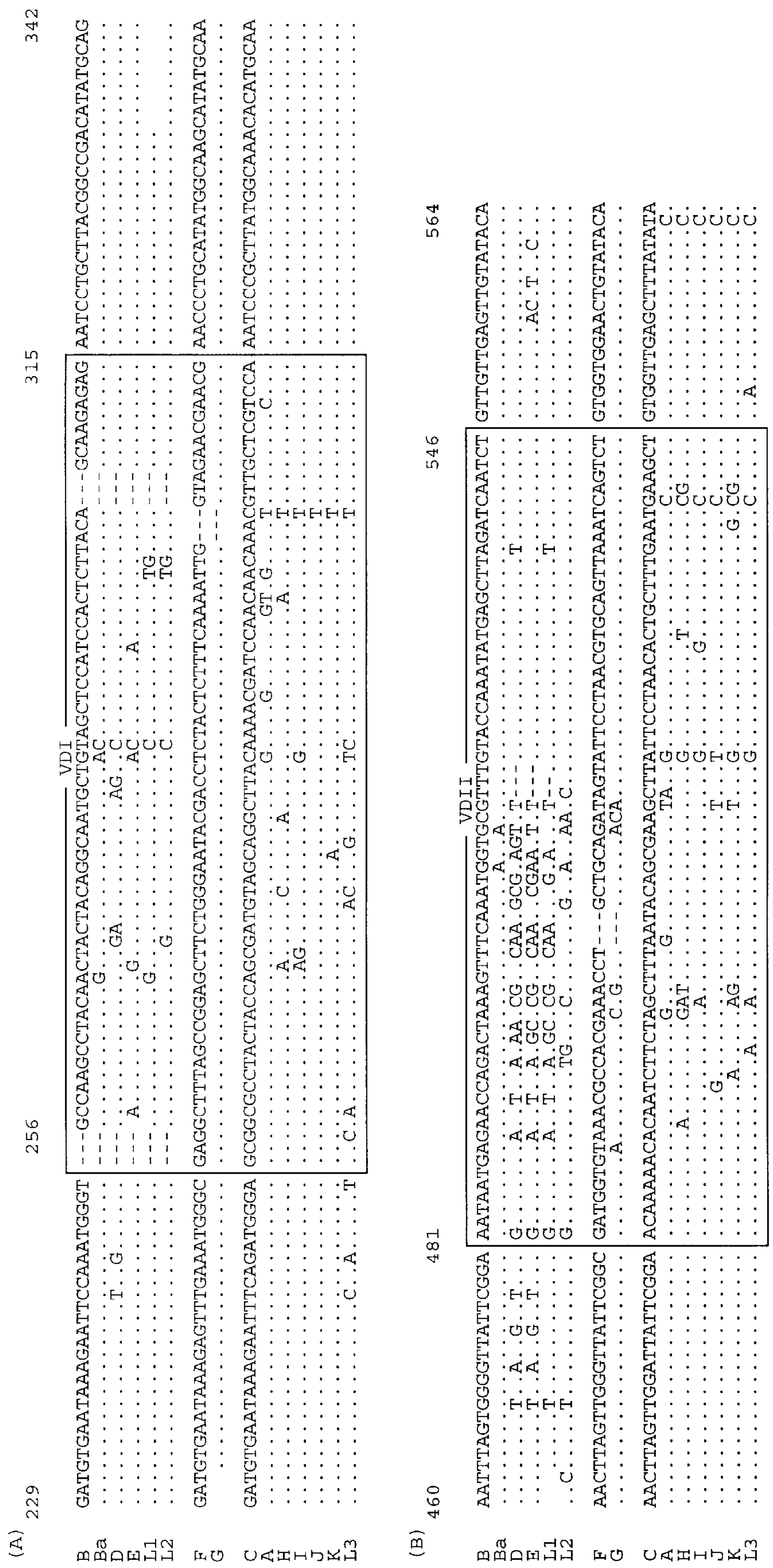
FIG. 3. (A, B, C and D) The nucleotide sequences of MOMP VDs I, II, III and IV, respectively, of the 15 *C. trachomatis* serovars. The boxed regions of the sequences identify each of the four VDs. Serovars B, F and C MOMP sequences were used as prototypes for comparative sequence analysis. The nucleotide positions shown are for serovar B MOMP. Exact nucleotide positions for other MOMP VD sequences differ slightly because of insertions and/or deletions within the VDs.
Figure 3B:
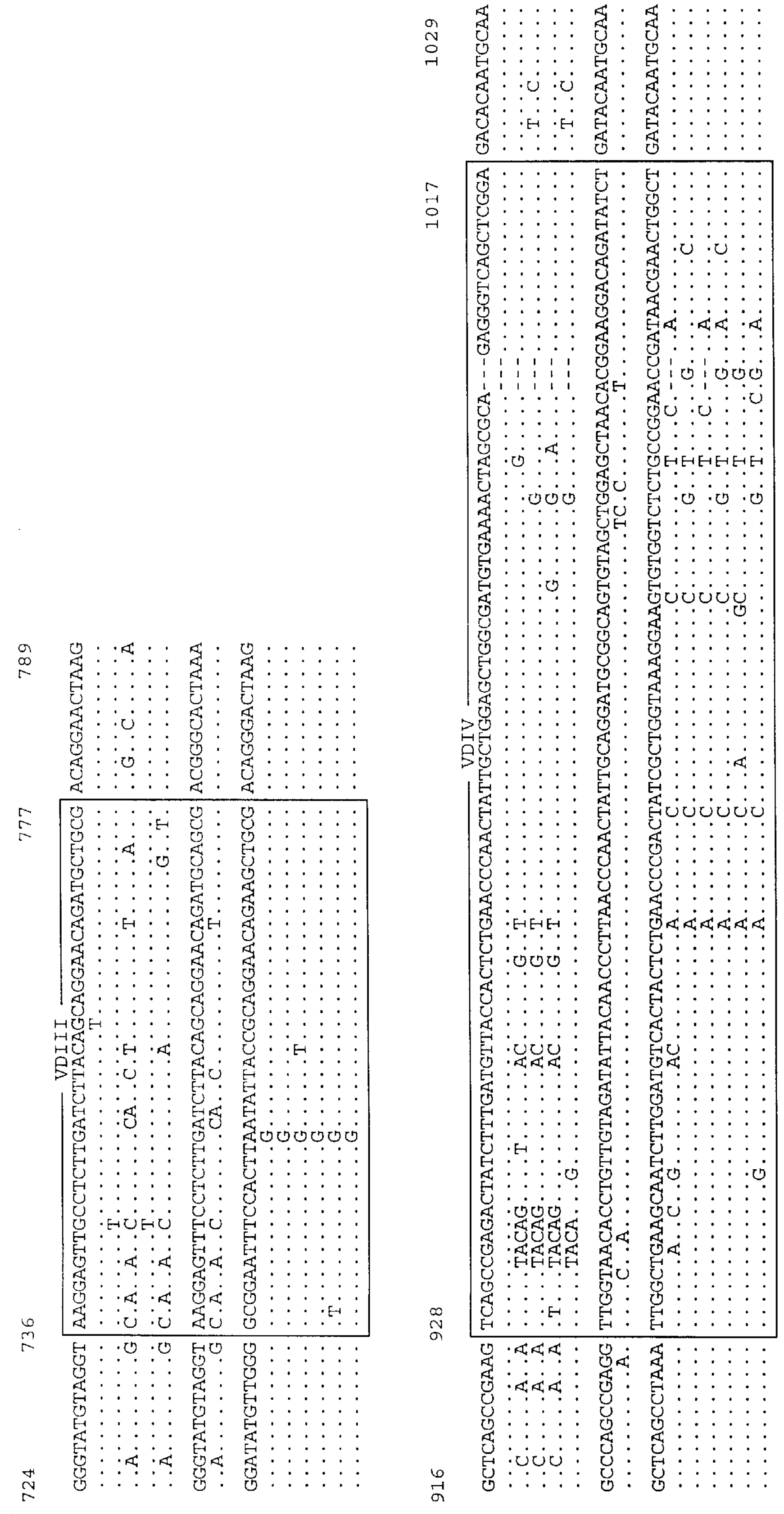

The synthetic oligonucleotides used for sequencing the MOMP VDs of the 15 *C. trachomatis* serovars are those depicted previously in Table 1. The location of the complementary sequences in the MOMP genes of serovars B, L2, A, C and F are shown in FIG. 3. All oligonucleotides were 21 mers and were complementary to conserved nucleotide sequences 40 to 60 nucleotides downstream (3') from the VD to be sequenced. Because inter-serogroup (but not intra-serogroup) nucleotide variation occurs within these regions, oligonucleotides complementary to serogroup specific MOMP sequences were constructed for use in the sequencing of the variable domains of the serovars within each serogroup. The 40 to 60 nucleotide distance between the VD and the downstream oligonucleotide primer site was necessary to produce high resolution sequences of the VDs.

The nucleotide and deduced amino acid sequences of the 4 variable domains for each of the 15 *C. trachomatis* serovars are individually depicted in FIGS. 5–19. These sequences are also presented comparatively in FIG. 3 (nucleotide sequences) and FIG. 4 (deduced amino acid sequences). The B, F and C serovars' MOMP VDs are used as prototype sequences for comparative analyses of serovar VDs within the B, intermediate and C serogroup, respectively. A discussion of the results of the comparative analyses of the nucleotide and amino acid sequences of the four VDs for each *C. trachomatis* serovar is presented below.

1. Variable Domain I

VDI contains 60 nucleotides encoding 20 amino acids for all B serogroup serovars, 66 nucleotides encoding 22 amino acids for serovars K, L3 and all C serogroup serovars, and 63 nucleotides encoding 21 amino acids for serovars F and G. The nucleotide sequences of VDIs from B serogroup serovars are highly conserved with only 3 to 5 substitutions per serovar as compared to the B serovar prototype sequence. The deduced amino acid sequences of VDIs of B serogroup serovars are also conserved with only 2 to 4 substitutions per serovar, with the majority of substitutions occurring within a 12 amino acid region (residues 68–79) that resides in the central portion of the domain.

In contrast to the above, serovars in the C serogroup and serovars K and L3 show greater nucleotide variation in VDI than the B serogroup. Compared to C VDI, the other C serogroup serovars have 1 to 9 nucleotide substitutions in VDI that result in 0 to 4 amino acid changes. As above, the majority of these substitutions occur in the central region of the domain.

VDIs of serovars F and G are identical in their nucleotide and amino acid sequences.

2. Variable Domain II

VDII contains 63 nucleotides encoding 21 amino acids in the MOMP of serovars D, E, L1, F and G. The VDIIs of the remaining 10 serovars each have 66 nucleotides encoding 22 amino acids. VDII shows more sequence variation than VDI in all serovars. As compared to serovar B, other B serogroup serovars have 2 to 19 nucleotide substitutions resulting in 2 to 8 amino acid changes. The least amount of variation occurs between serovars B and Ba in which there are two nucleotide substitutions that each result in an amino acid substitution. Most of the amino acid substitutions occur within an 8 amino acid region in the central part of the domain (residues 144 to 151).

The VDIIs of C serogroup serovars show considerable sequence variation having 4 to 8 nucleotide substitutions which result in 3 to 6 amino acid changes. A similar amount of variation was found in VDII sequences between the F and G serovars of the intermediate serogroup. Compared to serovar F VDII sequences, serovar G VDII has 6 nucleotide substitutions resulting in 3 amino acid changes.

3. Variable Domain III

VDIII is the smallest and least variable of the four domains. VDIII contains 42 nucleotides which encode 14 amino acids. The VDIII sequences of A, H, J and L3 are identical to each other. Serovars D, L1 and F have identical sequences which differ from serovar B by 3 amino acid substitutions. The remaining serovars have sequences differing from serovar B by 1 to 4 amino acid substitutions.

4. Variable Domain IV

VDIV is the largest variable domain containing 96 nucleotides encoding 32 amino acids in serovars A, I and all B serogroup serovars, and 99 nucleotides encoding 33 amino acids in the remaining serovars. The VDIV domain can be separated into three distinct regions based on sequence homology:

(i) the N-terminal region (residues 288–295), (ii) the central region (residues 296–306), and (iii) the C-terminal region (residues 307–317).

Using micro-immunofluorescence polyclonal mouse sera, the 15 serovars have been separated into three serogroups. Group 1 or the B serogroup contains serovars B, Ba, D, E, L1 and L2; group 2, the intermediate serogroup, serovars F and G; and group 3, the C serogroup serovars A, C, H, I, J, K and L3.

Within the B serogroup, serovars B and Ba have identical sequences in the N-terminal regions, as do serovars D and E. There are three amino acid substitutions between serovars B-Ba and D-E. Serovars L1 and L2 contain one and two additional amino acid substitutions in this region, respectively. Within the C serogroup, serovars C, H, I, J and K have identical sequences in the N-terminal region of VDIV. Serovar L3 contains a single amino acid substitution. Serovar A contains the most variable sequence in this region, containing 4 sequence substitutions as compared to the prototype C serovar sequence. Serovars F and G differ in this region by two amino acids.

The central region of VDIV is the most highly conserved sequence among the VDs of the chlamydial serovars. A nine amino acid sequence (TTLNPTIAG) is conserved in all serovars except serovar K, which contains a threonine (T) instead of an alanine (A) (residue 303). The central NPT sequence in VDIV is present in all 15 serovars.

The C-terminal region of VDIV is highly conserved among the B serogroup servars. In contrast, this region of VDIV in C serogroup serovars shows a significant amount of amino acid variation, although the amino acid composition is similar (predominately S, T, E and A). Serovars F and G differ by three amino acid residues in this region.

In contrast to the historical classification noted above, wherein serovars K and L3 are placed within the C serogroup, immunotyping with monoclonal antibodies specific to MOMP has been recently employed and serovars K and L3 have been reclassified to the intermediate serogroup. Based on the present invention and comparative MOMP VD amino acid homology analysis, however, serovars K and L3 clearly belong in the historical C serogroup.

C. Inter- and Intra-serogroup Amino Acid Homologies

The percent of amino acid homology and the total number of amino acid substitutions for the VDs of each serovar are shown in Table 2.

TABLE 2

Comparative amino acid homologies of MOMP VDs of the 15 *C. trachomatis* serovars[a]

| | B | Ba | D | E | L1 | L2 | F | G | C | A | H | I | J | K | L3 |
|---|---|---|---|---|---|---|---|---|---|---|---|---|---|---|---|
| B | 100[a] | 94.2 | 80.2 | 76.7 | 77.9 | 77.9 | 43.7 | 42.5 | 38.2 | 40.9 | 40.4 | 43.2 | 42.7 | 42.7 | 41.6 |
| | (0)[c] | (5) | (17) | (20) | (19) | (19) | (49) | (50) | (55) | (52) | (53) | (50) | (51) | (51) | (52) |
| Ba | | 100 | 77.9 | 76.7 | 76.7 | 76.7 | 43.7 | 43.7 | 37.1 | 39.8 | 39.3 | 42 | 41.6 | 41.6 | 40.4 |
| | | (0) | (19) | (20) | (20) | (20) | (49) | (49) | (56) | (53) | (54) | (51) | (52) | (52) | (53) |
| D | | | 100 | 82.4 | 85.9 | 76.7 | 44.8 | 43.7 | 38.2 | 42.7 | 39.3 | 42 | 41.6 | 40.4 | 41.6 |
| | | | (0) | (15) | (12) | (20) | (48) | (49) | (55) | (51) | (54) | (51) | (52) | (53) | (52) |
| E | | | | 100 | 82.4 | 76 | 39.1 | 43.7 | 40.4 | 43.2 | 40.2 | 42 | 43.8 | 41.6 | 43.8 |
| | | | | (0) | (15) | (21) | (53) | (49) | (53) | (50) | (53) | (51) | (50) | (52) | (50) |
| L1 | | | | | 100 | 77.3 | 44.8 | 44.8 | 40.4 | 43.2 | 42.7 | 44.3 | 46.1 | 41.6 | 42.7 |
| | | | | | (0) | (20) | (48) | (48) | (53) | (50) | (51) | (49) | (48) | (52) | (51) |
| L2 | | | | | | 100 | 40.2 | 42.2 | 36 | 39.8 | 39.3 | 42 | 40.4 | 38.2 | 43.8 |
| | | | | | | (0) | (52) | (50) | (57) | (53) | (54) | (51) | (53) | (55) | (50) |
| F | | | | | | | 100 | 85.1 | 34.8 | 37.5 | 36 | 34.1 | 37.1 | 32.6 | 39.3 |

TABLE 2-continued

Comparative amino acid homologies of MOMP VDs of the 15 *C. trachomatis* serovars[a]

| | B | Ba | D | E | L1 | L2 | F | G | C | A | H | I | J | K | L3 |
|---|---|---|---|---|---|---|---|---|---|---|---|---|---|---|---|
| | | | | | | | (0) | (13) | (58) | (55) | (57) | (58) | (56) | (60) | (54) |
| G | | | | | | | | 100 | 39.3 | 40.9 | 38.2 | 37.5 | 40.4 | 36 | 43.8 |
| | | | | | | | | (0) | (54) | (52) | (55) | (55) | (53) | (57) | (50) |
| C | | | | | | | | | 100 | 77.5 | 83.1 | 86.4 | 88.8 | 85.4 | 85.4 |
| | | | | | | | | | (0) | (20) | (15) | (12) | (12) | (10) | (13) |
| A | | | | | | | | | | 100 | 74.2 | 81.8 | 84.3 | 75.3 | 79.8 |
| | | | | | | | | | | (0) | (23) | (16) | (14) | (22) | (18) |
| H | | | | | | | | | | | 100 | 83 | 86.5 | 83.1 | 83.1 |
| | | | | | | | | | | | (0) | (15) | (12) | (15) | (15) |
| I | | | | | | | | | | | | 100 | 87.6 | 81.8 | 86.4 |
| | | | | | | | | | | | | (0) | (11) | (16) | (12) |
| J | | | | | | | | | | | | | 100 | 86.5 | 87.6 |
| | | | | | | | | | | | | | (0) | (12) | (11) |
| K | | | | | | | | | | | | | | 100 | 80.9 |
| | | | | | | | | | | | | | | (0) | (17) |
| L3 | | | | | | | | | | | | | | | 100 |
| | | | | | | | | | | | | | | | (0) |

[a]Amino acid sequences of the four VDs were used for calculating homologies.
[b]Percent homology.
[c]Number of amino acid substitutions.

Inter-group (1, 2 and 3) VD amino acid homology is between 33 and 46%. Intra-group VD amino acid homology was between 74 and 94% for groups 1 and 3, and 85% for group 2. Therefore, classification of *C. trachomatis* isolates based on MOMP VD amino acid homology correlates extremely well with the historical serological classification and generally with immunotyping using MOMP specific monoclonal antibodies (see e.g., Wang et al., supra). The present inventors note, however, that recent immunotyping using monoclonal antibodies places serovars K and L3 within the intermediate serogroup (serovars F and G), whereas VD amino acid homology comparison shows serovars K and L3 to be more closely related to serovars within the C serogroup.

III. Immunogenicity Based on Hydrophilicity and Charge Values

The VDs are hydrophilic and charged; properties indicating that these sequences are associated with the chlamydial cell surface and are potential antigenic sites. In fact, major antigenic sites which elicit the formation of protective serotyping antibodies have been mapped to VDI, VDII, and VDIV of the MOMP of serovars A, B, C and L2 (Baehr et al., supra). However, the antigenic properties of the VDs of the remaining 11 serovars have not as yet been described.

In order to define the antigenicity of these domains, the MOMP VDs of the chlamydial serovars were analyzed for hydrophilicity and charge using standard measurements and calculations. The number of charged amino acids and the hydrophilicity value of sequences within each MOMP VD for the 15 serovars was determined. These values are provided in Table 3.

TABLE 2

TABLE 3. The hydrophilicity values and charges of *C. trachomatis* MOMP VDs

| | VDI | | | VDII | | | VDIII | | | N' end VDIV | | | Middle | | | C' end of VDIV | | |
|---|---|---|---|---|---|---|---|---|---|---|---|---|---|---|---|---|---|---|
| | Basic[a] | Acidic[b] | HV[c] | Basic | Acidic | HV | Basic | Acidic | HV | Basic | Acidic | HV | Basic | Acidic | HV | Basic | Acidic | HV |
| B | 2 | 1 | +1.8 | 1 | 2 | +1.8 | 1 | 3 | +4.3 | 1 | 2 | +2.6 | 0 | 0 | −5.1 | 1 | 3 | +7.6 |
| Ba | 2 | 1 | +2.8 | 1 | 2 | +2.2 | 1 | 3 | +5.1 | 1 | 2 | +2.6 | 0 | 0 | −5.1 | 1 | 3 | +7.6 |
| D | 2 | 2 | +8.8 | 2 | 4 | +9.7 | 1 | 3 | +3.6 | 1 | 1 | +0.2 | 0 | 0 | −5.1 | 1 | 3 | +7.3 |
| E | 2 | 2 | +6.4 | 1 | 3 | +7.8 | 0 | 2 | −3.8 | 1 | 1 | +0.2 | 0 | 0 | −5.1 | 1 | 3 | +7.5 |
| L1 | 2 | 1 | +3.5 | 2 | 4 | +12.5 | 1 | 3 | +3.6 | 1 | 1 | −1.9 | 0 | 0 | −5.1 | 1 | 3 | +7.9 |
| L2 | 2 | 1 | +3.5 | 1 | 4 | +7.7 | 1 | 3 | +3.7 | 1 | 1 | −0.5 | 0 | 0 | −5.1 | 1 | 3 | +7.5 |
| AVG[d] | 2 | 1.3 | +4.47 | 1.35 | 3.2 | +6.95 | 0.8 | 2.8 | +2.75 | 1 | 1.3 | +0.53 | 0 | 0 | −5.1 | 1 | 3 | +7.57 |
| F | 2 | 2 | +3.5 | 1 | 2 | +2.1 | 1 | 3 | +3.6 | 1 | 2 | −2.5 | 0 | 0 | −5.1 | 0 | 2 | +1.3 |
| G | 2 | 2 | +3.5 | 0 | 2 | 0 | 0 | 2 | −2.8 | 2 | 1 | +1.9 | 0 | 0 | −5.1 | 0 | 2 | +0.6 |
| AVG[e] | 2 | 2 | +3.5 | 0.5 | 2 | +1.05 | 0.5 | 2.5 | +4.4 | 1.5 | 1.5 | −0.3 | 0 | 0 | −5.1 | 0 | 2 | +0.95 |
| C | 1 | 2 | +1.5 | 2 | 1 | −0.3 | 0 | 2 | −2.7 | 1 | 2 | +1.1 | 0 | 0 | −5.1 | 1 | 3 | +6.6 |
| A | 2 | 3 | +5.9 | 1 | 1 | −3.1 | 0 | 3 | +0.1 | 2 | 1 | +3.0 | 0 | 0 | −5.1 | 1 | 3 | +6.6 |
| H | 2 | 3 | +8.8 | 4 | 1 | +5.7 | 0 | 3 | +0.1 | 1 | 2 | +1.1 | 0 | 0 | −5.1 | 1 | 3 | +6.6 |
| I | 2 | 3 | +7.0 | 2 | 0 | −0.1 | 0 | 3 | −1.2 | 1 | 2 | +1.1 | 0 | 0 | −5.1 | 1 | 3 | +6.6 |
| J | 1 | 2 | +1.5 | 1 | 0 | −7.4 | 0 | 3 | +0.1 | 1 | 2 | +1.1 | 0 | 0 | −5.1 | 1 | 3 | +6.6 |

TABLE 2-continued

TABLE 3. The hydrophilicity values and charges of *C. trachomatis* MOMP VDs

| | VDI | | | VDII | | | VDIII | | | N' end VDIV | | | Middle | | | C' end of VDIV | | |
|---|---|---|---|---|---|---|---|---|---|---|---|---|---|---|---|---|---|---|
| | Basic[a] | Acidic[b] | HV[c] | Basic | Acidic | HV | Basic | Acidic | HV | Basic | Acidic | HV | Basic | Acidic | HV | Basic | Acidic | HV |
| K | 1 | 3 | +6.5 | 2 | 2 | +0.1 | 0 | 3 | −0.9 | 1 | 2 | +1.1 | 0 | 0 | −5.0 | 1 | 3 | +7.3 |
| L3 | 1 | 3 | +6.2 | 2 | 0 | −3.6 | 0 | 3 | +0.1 | 1 | 2 | +1.4 | 0 | 0 | −5.1 | 1 | 3 | +7.3 |
| AVG[f] | 1.4 | 2.7 | +5.3 | 2 | 0.7 | −1.24 | 0 | 2.9 | −0.63 | 1.1 | 1.9 | +1.4 | 0 | 0 | −5.1 | 1 | 3 | +6.8 |

[a]Total number of histidines, arginines and lysines.
[b]Total number of aspartic acids and glutamic acids.
[c]HV = hydrpholicity value assigned by Hopp and Woods, Proc. Natl. Acad. Sci. USA 78:3824–2828 (1981)
[d]Average charge and HV for the B serogroup.
[e]Average charge and HV for the intermediate serogroup.
[f]Average charge and HV for the C serogroup.

As the data demonstrates, the VDs have a broad range of hydrophilicity and charge. The VDI sequences of serovars in the B serogroup had an average hydrophilicity value of 4.47, and contained an average of 2 positive (basic) charges and 1.3 negative (acidic) charges, while the VDII sequences had an average hydrophilicity value roof 6.95, and contained an average of 1.35 positive charges and 3.2 negative charges. Based on these results, the VDII sequences of serovars within the B serogroup are predicated to have the greater immunogenic potential between the two.

Indeed, as reported by Stephens et al. (J. Exp. Med., supra) epitope mapping studies using antisera prepared against synthetic peptides corresponding to MOMP VDs show that serovar-specific determinants are located in the VDII of the MOMP of serovars B, C and L2, and a highly conserved species-specific MOMP determinant is mapped to VDIV as depicted in Table 4.

As with the C serogroup, the MOMP VDI sequences of the intermediate serovars F and G were more hydrophilic and charged than the VDII sequences. Several serovars (D, E and H) contain both VDI and VDII sequences which are extremely hydrophilic and charged, suggesting that in MOMPs of these serovars, both domains may be immunogenic.

Although antigenic sites have not yet been mapped to VDIII, its hydrophilicity and charge values implicate this domain as a potential immunogenic site as well.

As noted previously, VDIV has been divided into three regions, (i) N-terminal (residues 284–295), central (residues 296–306) and C-terminal (residues 307–317). The hydrophilicity and charge for each region has been independently calculated.

The VDIV domain shows a consistent pattern of hydrophilicity and charge in each region for MOMPs of all serovars. The N-terminal region is charged but is weakly hydrophilic; the central region is consistently uncharged and is hydrophobic; and the C-terminal region is both highly charged and hydrophilic, with the exception of serovars F and G which have only moderate charge and hydrophilicity.

TABLE 4

The charge and hydrophilicity value of epitopes on *C. trachomatis* MOMP mapped by MAbs

| Monoclonal antibody | Sequence of epitope[a] | Amino Acids Basic | Amino Acids Acidic | Hydrophilicity value | Location of epitope |
|---|---|---|---|---|---|
| A-20 | D—V—A—G—L—E—K—D—P—V | 1 | 3 | +4.1 | A-VDI |
| L21-45 | D—N—E—N—H—A—T—V—S—D—S—K—L—V | 2 | 3 | +6.8 | L2-VDII |
| B-B6 | N—N—E—N—Q—T—K—V—S—N—G—A—F—V | 1 | 1 | +0.9 | B-VDII |
| B-B5 | P—T—I—A—G—A—G—D—V—K—T—S—A—E—G | 1 | 2 | +3.8 | B-VDIV C-terminus |
| L21-10 | T—T—L—N—P—T—I—A—G | 0 | 0 | −5.1 | VDIV of all serovars except K |

[a]Sequence of epitope as determined by lambda gt11 epitope mapping according to Baehr et al., supra.

In contrast to the above, VDI sequences of C serogroup serovars' MOMP were more hydrophilic and charged than VDII. The average hydrophilicity for VDI was 5.3 with 1.4 positive and 2.7 negative charges, while the hydrophilicity value for VDII was −1.24 with 2 positive and 0.7 negative charges. These data suggest that VDI sequences of C serovars have a greater immunogenic potential than VDII sequences. This conclusion is supported by the work of Baehr et al., supra, who, using a lambda-gt11 epitope mapping procedure showed that the serovar-specific MOMP epitope for serovar A and L2 mapped to VDI and VDII, respectively, whereas subspecies, serogroup and species-specific epitopes mapped to VDIV. Specifically, the epitope recognized by monoclonal antibody A-20, which is specific for serovar A MOMP has been mapped to VDI (Table 4).

The single exception in correlating hydrophilicity and charge with known MOMP antigenic determinants is the species-specific MOMP epitope recognized by monoclonal antibody L21-10. This epitope is located in the central region of VDIV (TTLNPTIAG) and is uncharged and strongly hydrophobic (−5.1). From the epitope data, it appears that serovar-specific determinants are located in MOMP VDI, VDII or both, while common or serogroup-specific MOMP antigenic determinants are located in VDIV.

We claim:

1. An isolated polypeptide consisting of a variable domain, or a fragment thereof, of a major outer membrane protein (MOMP) of *Chlamydia trachomatis* serovar Ba, wherein said variable domain comprises:

(a) AKPTATTGNATAPSTLTARE;

(b) NNENQTKVSNSTFVPNMSLDQS;

(c) KELPLDLTSGTDAA; or (d) SAETIFDVTTLNPTIAGAGDVKTSAEGQLG.

2. An isolated polypeptide consisting of a variable domain, or a fragment thereof, of a major outer membrane protein (MOMP) of *Chlamydia trachomatis* serovar D, wherein said variable domain comprises:

(a) AKPTTDTGNSAAPSTLTARE;

(b) DNENQKTVKAESVPNMSFDQS;

(c) KEFPLDLTAGTDAA; or (d) SATAIFDTTTLNPTIAGAGDVKTGAEGQLG.

3. An isolated polypeptide consisting of a variable domain, or a fragment thereof, of a major outer membrane protein (MOMP) of *Chlamydia trachomatis* serovar E, wherein said variable domain comprises:

(a) DKPTSTTGNATAPTTLTARE, (b) DNENQSTVKTNSVPNMSLDQS;

(c) QEFPLALIAGTDAA; or (d) SATAIFDTTTLNPTIAGAGDVKASAEGQLG.

4. An isolated polypeptide consisting of a variable domain, or a fragment thereof, of a major outer membrane protein (MOMP) of *Chlamydia trachomatis* serovar F, wherein said variable domain comprises:

(a) EALAGASGNTTSTLSKLVERT;

(b) DGVNATKPAADSIPNVQLNQS;

(c) KEFPLDLTAGTDAA; or (d) LVTPVVDITTLNPTIAGCGSVAGANTEGQIS.

5. An isolated polypeptide consisting of a variable domain, or a fragment thereof, of a major outer membrane protein (MOMP) of *Chlamydia trachomatis* serovar G, wherein said variable domain comprises:

(a) EALAGASGNTTSTLSKLVERT;

(b) DGENATQPAATSIPNVQLNQS;

(c) QEFPLALTAGTDAA; or (d) LAKPVVDITTLNPTIAGCGSVVMNSEGQIS.

6. An isolated polypeptide consisting of a variable domain, or a fragment thereof, of a major outer membrane protein (MOMP) of *Chlamydia trachomatis* serovar H, wherein said variable domain comprises:

(a) AAPTTNDAADLQNDPKTNVARP;

(b) TKTKSSDFNTAKLVPNIALNRA;

(c) AEFPLDITAGTEAA; or (d) LAEAILDVTTLNPTIAGKGTVVASGSDNDLA.

7. An isolated polypeptide consisting of a variable domain, or a fragment thereof, of a major outer membrane protein (MOMP) of *Chlamydia trachomatis* serovar I, wherein said variable domain comprises:

(a) AAPTTKDVAGLENDPTTNVARP;

(b) TKTQSSNFNTAKLVPNAALNQA;

(c) AEFPLDIIAGTEAA; or (d) LAEAILDVTTLNPTIAGKGTVVSSAENELA.

8. An isolated polypeptide consisting of a variable domain, or a fragment thereof, of a major outer membrane protein (MOMP) of *Chlamydia trachomatis* serovar J, wherein said variable domain comprises:

(a) AAPTTSDVAGLQNDPTTNVARP;

(b) TKTQASSFNTANLFPNTALNQA;

(c) AEFPLDITAGTEAA; or (d) LAEAILDVTTLNPTIAGKGTVVASGSENDLA.

9. An isolated polypeptide consisting of a variable domain, or a fragment thereof, of a major outer membrane protein (MOMP) of *Chlamydia trachomatis* serovar K, wherein said variable domain comprises:

(a) AAPTTSDVEGLQNDPTTNVARP;

(b) TKTQYSKFNTANLVPNTALDRA;

(c) VEFPLDITAGTEAA; or (d) LAEAILDVTTLNPTITGKGAVVSSGSDNELA.

10. An isolated polypeptide consisting of a variable domain, or a fragment thereof, of a major outer membrane protein (MOMP) of *Chlamydia trachomatis* serovar L3, wherein said variable domain comprises:

(a) AEPTTSDTAGLSNDPTTNVARP;

(b) TKTQSTNFNTAKLVPNTALNQA;

(c) AEFPLDITAGTEAA; or (d) LAEAVLDVTTLNPTIAGKGSVVASGSENELA.

11. An isolated DNA fragment encoding a variable domains or a fragment thereof, of a major outer membrane protein (MOMP) of *Chlamydia trachomatis* serovar Ba comprising one of the following nucleotide sequences:

(a) GCCAAGCCTACAGCTACTACAGGCAATGCTACAGCTCCATCCACTCTTACAGCAAGAGAG;

(b) AATAATGAGAACCAGACTAAAGTTTCAAATAGTACGTTTGTACCAAATATGAGCTTAGATCAATCT;

(c) AAGGAGTTGCCTCTTGATCTTACATCAGGAACAGATGCTGCG; OR (d) TCAGCCGAGACTATCTTTGATGTTACCACTCTGAACCAACTATTGCTGGAGCTGGCGATGTGAAAACTAGCGCAGAGGGTCAGCTCGGA.

12. An isolated DNA fragment encoding a variable domain, or a fragment thereof, of a major outer membrane protein (MOMP) of *Chlamydia trachomatis* serovar D comprising one of the following nucleotide sequences:

(a) GCCAAGCCTACAACTGATACAGGCAATAGTGCAGCTCCATCCACTCTTACAGCAAGAGAG;

(b) GATAATGAAAATCAAAAAACGGTCAAAGCGGAGTCTGTACCAAATATGAGCTTTGATCAATCT;

(c) AAGGAGTTTCCTCTTGATCTTACAGCAGGAACAGATGCTGCG; OR (d) TCAGCTACAGCTATTTTTGATACTACCACGCTTAACCCAACTATTGCTGGAGCTGGCGATGTGAAAACTGGCGCAGAGGGTCAGCTCGGA.

13. An isolated DNA fragment encoding a variable domain, or a fragment thereof, of a major outer membrane protein (MOMP) of *Chlamydia trachomatis* serovar E comprising one of the following nucleotide sequences:

(a) GACAAGCCTACAAGTACTACAGGCAATGCTACAGCTCCAACCACTCTTACAGCAAGAGAG;

(b) GATAATGAAAATCAAAGCACGGTCAAAACGAATTCTGTACCAAATATGAGCTTAGATCAATCT;

(c) CAAGAATTCCCTCTTGCACTCATAGCAGGAACTGATGCAGCG; or (d) TCAGCTACAGCTATCTTTGATACTAC-CACGCTTAACCCAACTATTGCTG-GAGCTGGCGATGTGAAAGCTAGCGCA-GAGGGTCAGCTCGGA.

14. An isolated DNA fragment encoding a variable domain, or a fragment thereof, of a major outer membrane protein (MOMP) of *Chlamydia trachomatis* serovar F comprising one of the following nucleotide sequences:

(a) GAGGCTTTAGCCGGAGCTTCTGG-GAATACGACCTCTACTCTTTCAAAATTG-GTAGAACGAACG;

(b) GATGGTGTAAACGCCACGAAACCTGCTG-CAGATAGTATTCCTAACGTGCAGT-TAAATCAGTCT;

(c) AAGGAGTTTCCTCTTGATCTTACAGCAG-GAACAGATGCAGCG; OR (d) TTGGTAACACCTGTTGTAGATATTA-CAACCCTTAACCCAACTATTGCAGGAT-GCGGCAGTGTAGCTGGAGCTAACACG-GAAGGACAGATATCT.

15. An isolated DNA fragment encoding a variable domain, or a fragment thereof, of a major outer membrane protein (MOMP) of *Chlamydia trachomatis* serovar G comprising one of the following nucleotide sequences:

(a) GAGGCTTTAGCCGGAGCTTCTGG-GAATACGACCTCTACTCTTTCAAAATTG-GTAGAACGAACG;

(b) GATGGTGAAAACGCCACGCAGCCTGCTG-CAACAAGTATTCCTAACGTGCAGT-TAAATCAGTCT;

(c) CAAGAATTCCCTCTTGCACTCACAGCAG-GAACTGATGCAGCG; or (d) TTGGCAAAACCTGTTGTAGATATTACA-CACCTTAACCCAACTATTGCAGGATGCG-GCAGTGTAGTCGCAGCTAACTCGGAAG-GACAGATATCT.

16. An isolated DNA fragment encoding a variable domains or a fragment thereof, of a major outer membrane protein (MOMP) of *Chlamydia trachomatis* serovar H comprising one of the following nucleotide sequences:

(a) GCGGCGCCTACTACCAACGATGCAGCA-GACTTACAAAACGATCCAAAAACAAAAT-GTTGCTCGTCCA;

(b) ACAAAAACAAAATCTTCTGATTTTAATA-CAGCGAAGCTTGTTCCTAACAT-TGCTTTGAATCGAGCT;

(c) GCGGAATTTCCACTTGATATTACCGCAG-GAACAGAAGCTGCG; or (d) TTGGCTGAAGCAATCTTGGATGTCAC-TACTCTAAACCCGACCATCGCTGG-TAAAGGAACTGTGGTCGCTTCCGGAAGC-GATAACGACCTGGCT.

17. An isolated DNA fragment encoding a variable domain, or a fragment thereof, of a major outer membrane protein (MOMP) of *Chlamydia trachomatis* serovar I comprising one of the following nucleotide sequences:

(a) GCGGCGCCTACTACCAAGGATGTAGCAG-GCTTAGAAAACGATCCAACAACAAATGT-TGCTCGTCCA;

(b) ACAAAAACACAATCTTCTAACTTTAATA-CAGCGAAGCTTGTTCCTAACGCT-GCTTTGAATCAAGCT;

(c) GCGGAATTTCCACTTGATATTATCGCAG-GAACAGAAGCTGCG; or (d) TTGGCTGAAGCAATCTTGGATGTCAC-TACTCTAAACCCGACCATCGCTGG-TAAAGGAACTGTGGTCTCTTCCGCA-GAAAACGAACTGGCT.

18. An isolated DNA fragment encoding a variable domain, or a fragment thereof, of a major outer membrane protein (MOMP) of *Chlamydia trachomatis* serovar J comprising one of the following nucleotide sequences:

(a) GCGGCGCCTACTACCAGCGATGTAGCAG-GCTTACAAAACGATCCAACAACAAATGT-TGCTCGTCCA;

(b) ACAAAAACACAAGCTTCTAGCTTTAATA-CAGCGAATCTTTTTCCTAACACT-GCTTTGAATCAAGCT;

(c) GCGGAATTTCCACTTGATATTACCGCAG-GAACAGAAGCTGCG; or (d) TTGGCTGAAGCAATCTTGGATGTCAC-TACTCTAAACCCGACCATCGCTGG-TAAAGGAACTGTGGTCGCTTCCGGAAGC-GAAAACGACCTGGCT.

19. An isolated DNA fragment encoding a variable domain, or a fragment thereof, of a major outer membrane protein (MOMP) of *Chlamydia trachomatis* serovar K comprising one of the following nucleotide sequences:

(a) GCGGCGCCTACTACCAGCGATGTAGAAG-GCTTACAAAACGATCCAACAACAAATGT-TGCTCGTCCA;

(b) ACAAAAACACAATATTCTAAGTTTAATA-CAGCGAATCTTGTTCCTAACACT-GCTTTGGATCGAGCT;

(c) GTGGAATTTCCACTTGATATTACCGCAG-GAACAGAAGCTGCG; or (d) TTGGCTGAAGCAATCTTGGATGTCAC-TACTCTAAACCCGACCATCACTGG-TAAAGGAGCTGTGGTCTCTTCCGGAAGC-GATAACGAACTGGCT.

20. An isolated DNA fragment encoding a variable domain, or a fragment thereof, of a major outer membrane protein (MOMP) of *Chlamydia trachomatis* serovar L3 comprising one of the following nucleotide sequences:

(a) GCCGAGCCTACTACCAGCGATA-CAGCGGGCTTATCAAACGATCCAACAA-CAAATGTTGCTCGTCCA;

(b) ACAAAAACACAATCTACTAACTTTAATA-CAGCGAAGCTTGTTCCTAACACT-GCTTTGAATCAAGCT;

(c) GCGGAATTTCCACTTGATATTACCGCAG-GAACAGAAGCTGCG; or (d) TTGGCTGAAGCAGTCTTGGATGTCAC-TACTCTAAACCCGACCATCGCTGG-TAAAGGAAGTGTGGTCGCTTCCGGCAGC-GAAAACGAACTGGCT.

* * * * *

UNITED STATES PATENT AND TRADEMARK OFFICE
CERTIFICATE OF CORRECTION

PATENT NO. : 5,869,608

DATED : February 9, 1999

INVENTOR(S): Caldwell et al.

It is certified that error appears in the above-identified patent and that said Letters Patent is hereby corrected as shown below:

In Claim 11, line 23, replace "domains or" with "domain, or"

In Claim 14, line 17, replace "; OR" with "; or"

In Claim 16, line 40, replace "domains or" with "domain, or"

Signed and Sealed this

Twenty-ninth Day of May, 2001

*Attest:*

NICHOLAS P. GODICI

*Attesting Officer*

*Acting Director of the United States Patent and Trademark Office*